US009681632B2

(12) United States Patent
Avila et al.

(10) Patent No.: US 9,681,632 B2
(45) Date of Patent: Jun. 20, 2017

(54) LACTUCA SATIVA CULTIVAR RIVER ROAD

(71) Applicant: Central Valley Seeds, Inc., Salinas, CA (US)

(72) Inventors: Tony M. Avila, Salinas, CA (US); Adolfo S. Mederos, Salinas, CA (US)

(73) Assignee: Central Valley Seeds, Inc., Salinas, CA (US)

( * ) Notice: Subject to any disclaimer, the term of this patent is extended or adjusted under 35 U.S.C. 154(b) by 223 days.

(21) Appl. No.: 14/591,663

(22) Filed: Jan. 7, 2015

(65) Prior Publication Data

US 2016/0192609 A1   Jul. 7, 2016

(51) Int. Cl.
*A01H 5/12*   (2006.01)
(52) U.S. Cl.
CPC ........................ *A01H 5/12* (2013.01)
(58) Field of Classification Search
None
See application file for complete search history.

(56) References Cited

U.S. PATENT DOCUMENTS

| 7,534,941 B1 * | 5/2009 | Avila | A01H 5/12 |
| | | | 435/410 |
| 2014/0250544 A1 * | 9/2014 | Avila | A01H 5/12 |
| | | | 800/265 |

* cited by examiner

*Primary Examiner* — Ashley K Buran
(74) *Attorney, Agent, or Firm* — McKee, Voorhees & Sease, PLC

(57) ABSTRACT

According to the invention, there is provided a novel romaine lettuce cultivar, designated River Road. 'River Road' is described as a vigorous romaine cultivar recommended for the main lettuce growing regions of California and Arizona. It has light heavy head weight, with long wide leaves. This invention thus relates to the seeds of lettuce cultivar River Road, to the plants of lettuce cultivar River Road, to plant parts of lettuce cultivar River Road, to methods for producing a lettuce cultivar by crossing the lettuce cultivar River Road with another lettuce cultivar, and to methods for producing a lettuce cultivar containing in its genetic material one or more backcross conversion traits or transgenes and to the backcross conversion lettuce plants and plant parts produced by those methods.

26 Claims, 6 Drawing Sheets

LACTUCA SATIVA CULTIVAR RIVER ROAD

FIELD OF THE INVENTION

The present invention relates to the field of plant breeding. In particular, this invention relates to a new lettuce variety designated "River Road".

BACKGROUND OF THE INVENTION

Lettuce is an increasingly popular crop. Worldwide lettuce consumption continues to increase. As a result of this demand, there is a continued need for new lettuce varieties. In particular, there is a need for improved romaine lettuce varieties that exhibit improved size uniformity, increased head weight, early maturity, increased tip burn resistance, a light green or yellow color, increased bolting resistance, corky root-rot resistance and disease resistance.

The present invention relates to a new and distinctive cos or romaine lettuce (*Lactuca sativa* L.) variety designated River Road. All publications cited in this application are herein incorporated by reference.

Most cultivated forms of lettuce belong to the highly polymorphic species *Lactuca sativa* that is grown for its edible head and leaves. *Lactuca sativa* is in the Cichorieae tribe of the Asteraceae (Compositae) family. Lettuce is related to chicory, sunflower, aster, dandelion, artichoke and chrysanthemum. *Sativa* is one of about 300 species in the genus *Lactuca*.

Presently, there are over a thousand known lettuce varieties within seven different morphological types. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce comes in many varieties, none of which form a head, and include the green oak leaf variety. The next three types are seldom seen in the United States: Latin lettuce looks like a cross between romaine and butterhead; stem lettuce has long, narrow leaves and thick, edible stems; and oilseed lettuce is a type grown for its large seeds that are pressed to obtain oil.

The romaine group of lettuces is characterized by large, cylindrical, semi-firm heads averaging 30.0 cm in diameter and 800 g in weight, which are borne on a set of frame leaves that form the base of the plant. The heads are composed of leaves that are spirally arranged on a stem with greatly foreshortened internodes, where the leaves are loosely clasping upon one another forming a roll of elongated, spatula-shaped (spatulate) leaves, where the length is normally 50% longer than the width, having a range of length to width ratios of 1.2 to 2.5, where 1.5 is most common. Romaine lettuces generally have a semi-open head formation. The name "romaine" comes from the French for "Roman". Outer leaves range in color intensity from dark green (RHS 146A) to mid-green (RHS 146B) to light green (RHS 146C) with inner leaves ranging from green (RHS 146B) to light green (RHS 146D). More information regarding the general characteristics of romaine lettuce may be found in Ryder, E. J., Leafy Salad Vegetables, AVI Publishing Company.

Romaine lettuce is *Lactuca sativa* L. var. longifolia Lam; also known as Cos. The plant develops in an upright open or upright compact growing habit with coarse textured leaves. The leaves are longer than they are wide, cupping together to form an elongated loose head. Leaf margins are often entire or undulated, rarely frilled. Outer leaves range in color from light green to dark green with a heavy midrib. Inner heart leaves are smaller and range from light yellow to light green in color.

Lettuce in general and leaf lettuce in particular is an important and valuable vegetable crop. Thus, a continuing goal of lettuce plant breeders is to develop stable, high yielding lettuce cultivars that are agronomically sound. To accomplish this goal, the lettuce breeder must select and develop lettuce plants with traits that result in superior cultivars.

Problems with existing cultivars adapted to western conditions include a lack of resistance to corky root rot. Corky root rot is believed to be caused by a pathogenic soil bacterium of the genus *Rhizomonas*. One species of *Rhizomonas* that is commonly found to cause corky root rot is *R. suberifaciens*. Corky root rot accounts for significant lettuce crop loss in the western United States, particularly in the valleys of the central coast of California, i.e., the Salinas, Santa Maria, and Lompoc valleys.

Corky root rot symptoms include yellow bands on tap and lateral roots of lettuce seedlings. Guide to Leafy Vegetable Production in the Far West, Ron Smith, ed., California-Arizona Farm Press (1997). Yellow areas gradually expand and develop a green-brown color with cracks and rough areas on the root surface. The entire taproot may become brown, severely cracked and may cease to function. Feeder root systems are reduced and damaged. Roots become very brittle and break off easily. When the root is severely discolored, above ground symptoms show up as wilting during warm temperatures, stunting and general poor, uneven growth. Loss of the root system results in stunted plants that are chlorotic and too small to harvest.

Additionally, color is a very important trait. Various shades of color can determine whether a food product is successful at market. A deeper shade of green looks more appetizing than a pale shade of green or a green with a yellowish tint. A deep green in a ripe, healthy head of lettuce is especially desirable in a Romaine lettuce and its varieties and has been found to be especially strong commercially.

There are numerous steps in the development of any novel, desirable plant germplasm. Plant breeding preferably begins with the analysis and definition of problems and weaknesses of the current germplasm, the establishment of program goals, and the definition of specific breeding objectives. The next step is preferably selection of germplasm that possess the traits to meet the program goals. The goal is to combine in a single variety or hybrid an improved combination of desirable traits from the parental germplasm.

For a further understanding of lettuce, its uses and history see Waycott et al, U.S. Pat. No. 5,973,232 and Subbaroa 1998, which are hereby incorporated by reference in their entirety.

The foregoing examples of the related art and limitations related therewith are intended to be illustrative and not exclusive. Other limitations of the related art will become apparent to those of skill in the art upon a reading of the specification.

SUMMARY OF THE INVENTION

According to the invention, there is provided a novel lettuce cultivar, designated River Road. The cultivar has a heavy head weight with long broad leaves. This invention thus relates to the seeds of lettuce cultivar River Road, to the plants of lettuce cultivar River Road, to plant parts of lettuce cultivar River Road, to methods for producing a lettuce cultivar produced by crossing the lettuce cultivar River Road with another lettuce cultivar, and to methods for producing a lettuce cultivar containing in its genetic material one or more backcross conversion traits or transgenes and to the backcross conversion lettuce plants and plant parts produced by those methods. This invention also relates to lettuce cultivars and plant parts derived from lettuce cultivar River Road, to methods for producing other lettuce cultivars derived from lettuce cultivar River Road and to the lettuce cultivars and their parts derived by the use of those methods. This invention further relates to lettuce cultivar seeds, plants and plant parts produced by crossing the lettuce cultivar River Road or a backcross conversion of River Road with another lettuce cultivar.

DETAILED DESCRIPTION OF THE INVENTION

Definitions

Figure 1:
FIG. 1 is a photograph of harvest mature River Road and Zuma lettuce plants. The photograph shows the larger size of River Road.
Figure 2:
FIG. 2 is a photograph of the Butt appearance of harvest mature River Road and Zuma lettuce plants. The photograph shows the larger size of River Road.
Figure 3:
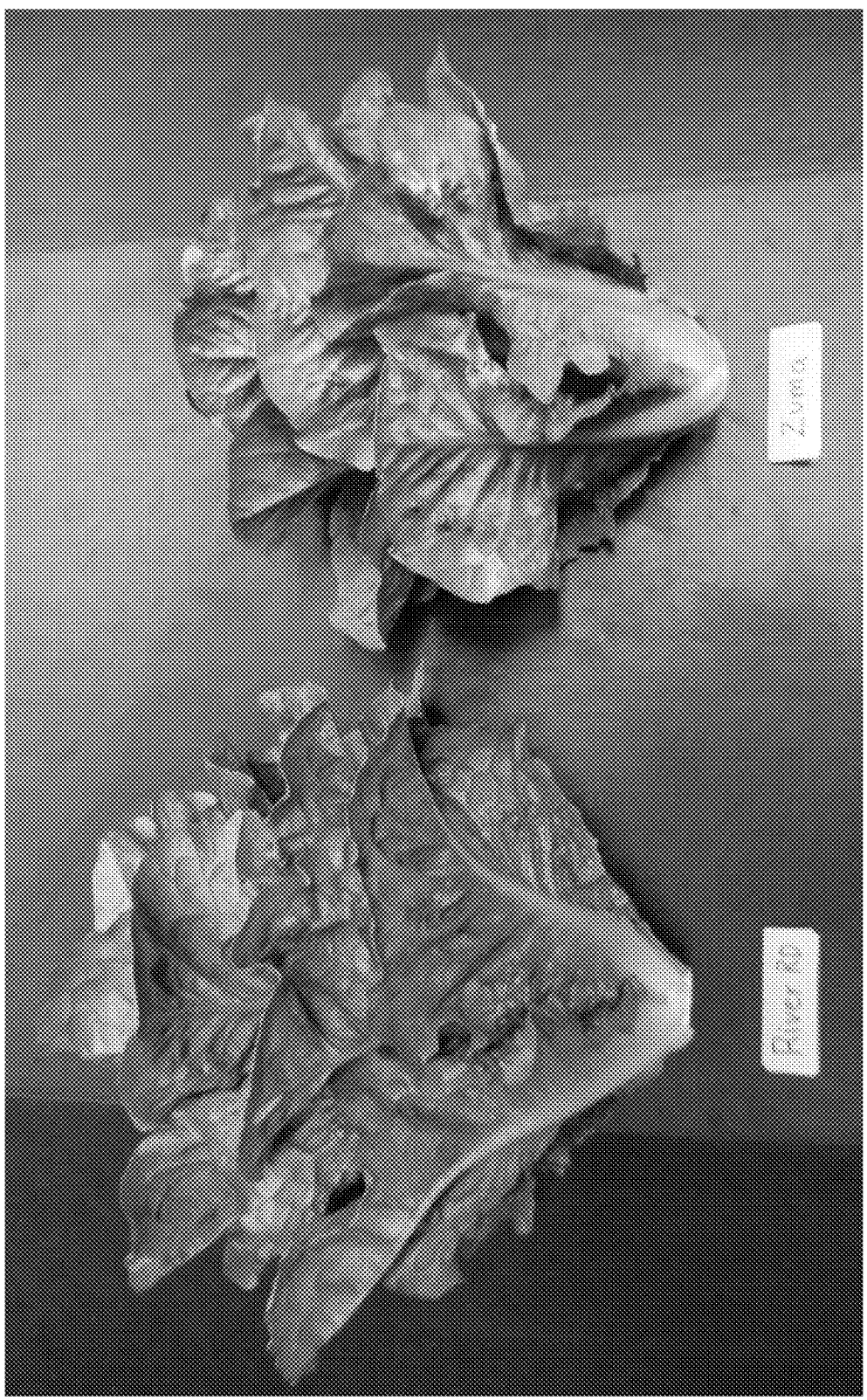
FIG. 3 is a photograph of harvest mature River Road and Zuma lettuce plants. Here again, the photograph demonstrates the larger size of River Road.
Figure 4A:
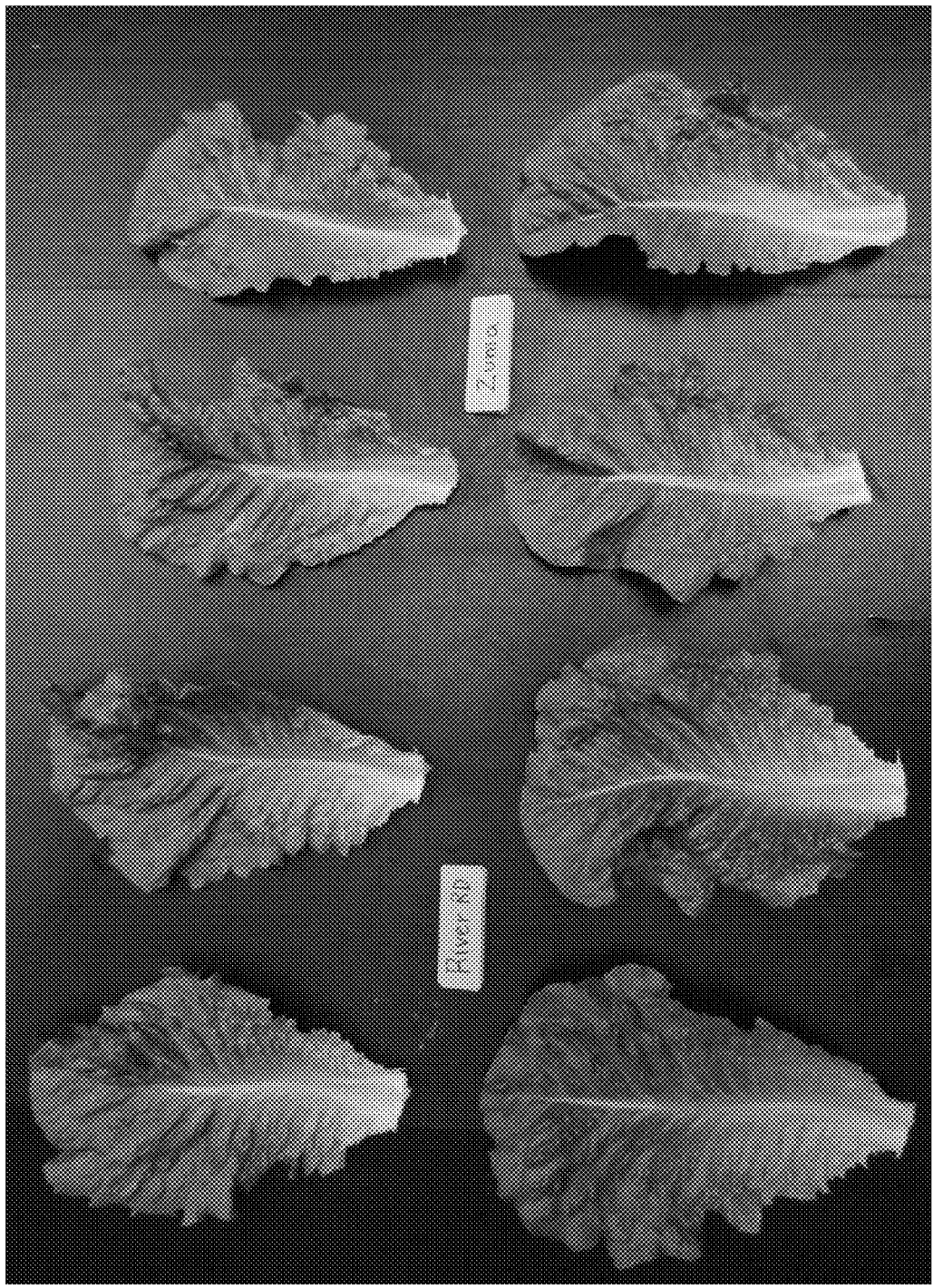
FIGS. 4A and 4B are photographs showing the harvest mature outer leaves of River Road and Zuma lettuce plants. The River Road outer leaves are significantly larger.
Figure 4B:
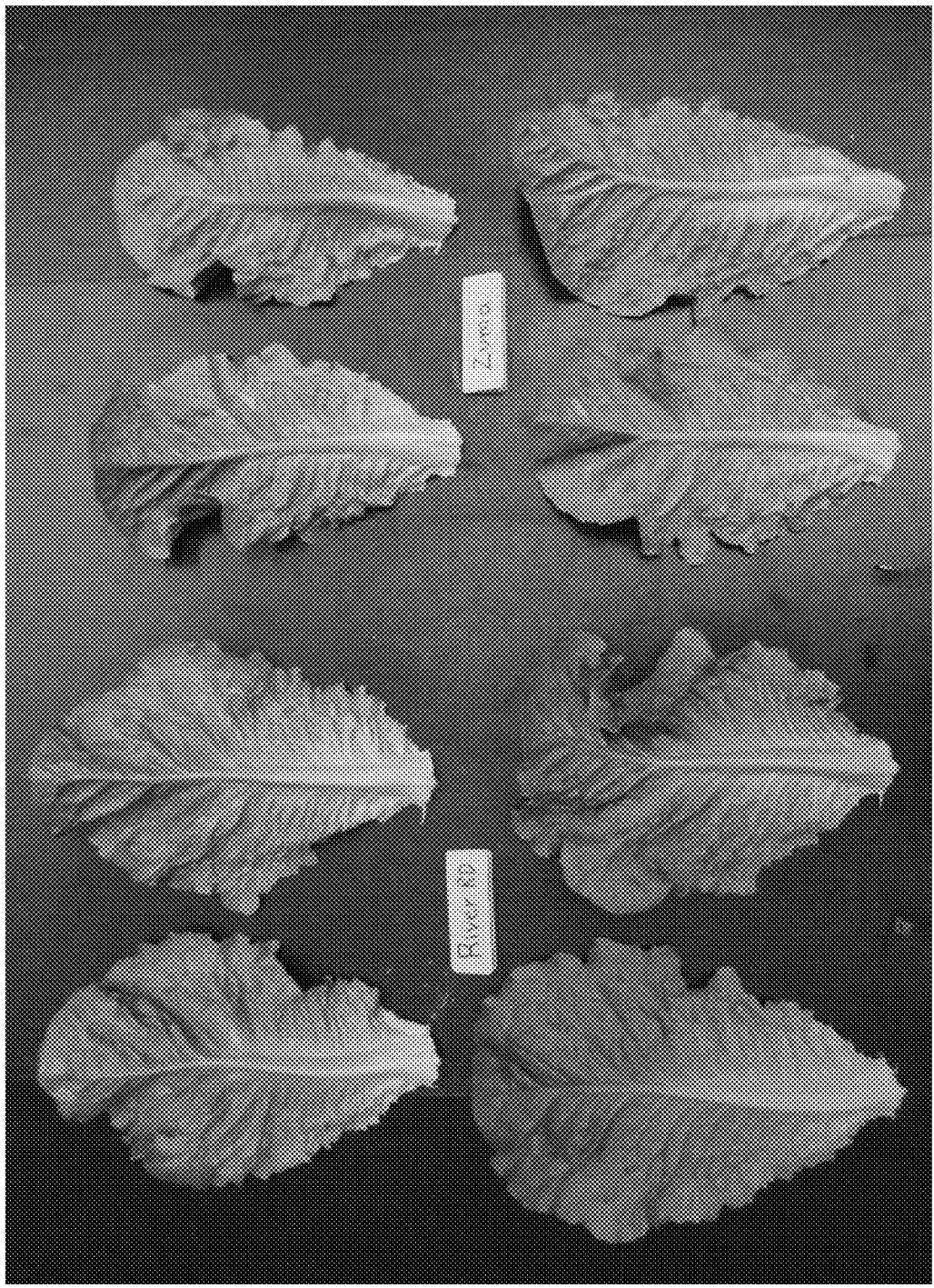
Figure 5:
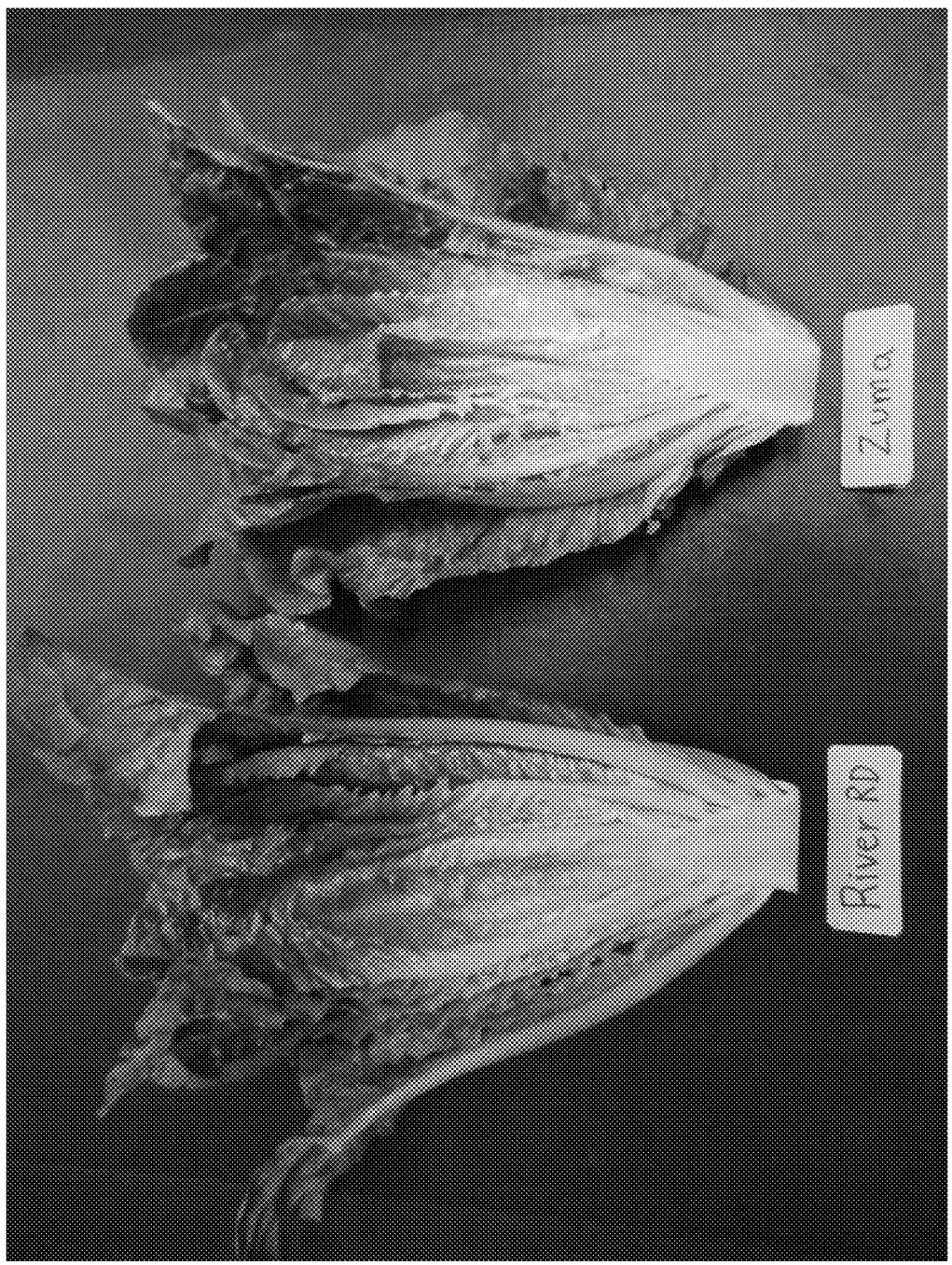
FIG. 5 is a photograph showing the interior and larger size of River Road compared to Zuma lettuce plants.

In the description and tables which follow, a number of terms are used. In order to provide a clear and consistent understanding of the present invention, the following definitions are provided:

Allele. The allele is any of one or more alternative forms of a genetic sequence. In a diploid cell or organism, the two alleles of a given genetic sequence occupy corresponding loci on a pair of homologous chromosomes.

Backcrossing. Backcrossing is a process in which a breeder crosses progeny back to one of the parents one or more times, for example, a first generation hybrid $F_1$ with one of the parental genotype of the $F_1$ hybrid.

Bolt. The process during which the stem within the lettuce head greatly elongates, causing the head to lose its shape and resulting ultimately in the producing of a flowering stalk.

Butt. The bottom portion of the lettuce which includes the stem and adjacent leaf bases of the outermost head leaves.

Core. The stem of the lettuce head on which the leaves are borne.

Core Length. Length of the internal lettuce stem, measured from the base of the cut head to the tip of the core.

Core Diameter. Diameter of the stem at the base of the cut head.

Core Value Coefficient. Calculated by taking the core length and multiplied by diameter which compares the core shapes. The larger the core volume coefficient value, the longer and narrower is the core. Inversely, the smaller the core volume coefficient number, the shorter and stubbier the core.

Cotyledon. In the case of lettuce, one of a pair of leaves formed on an embryo within a seed, which upon germination are the first leaves to emerge.

Essentially all the physiological and morphological characteristics. A plant having essentially all the physiological and morphological characteristics means a plant having the physiological and morphological characteristics of the recurrent parent, except for the characteristics derived from the converted gene.

First outer leaf. As described herein, "first outer leaf" means the first leaf located on the outer surface of the lettuce head.

First water date. The date the seed first receives adequate moisture to germinate. This can and often does equal the planting date.

Fourth Leaf. The fourth leaf formed on the lettuce plantlet subsequent to the emergence of the cotyledons.

Frame Diameter. A horizontal measurement of the plant diameter at its widest point, from outer most leaf tip to outermost leaf tip.

Frame Leaf. The first set of freely recurring leaves which are external to the head.

Head diameter. Diameter of the market cut and trimmed head with single cap leaf.

Head weight. The weight of a marketable lettuce head, cut and trimmed to market specifications.

Leaf area coefficient. Comparison of leaf areas or size between multiple varieties. This is calculated by multiplying the leaf width by the leaf length.

Leaf Index. Comparison of leaf shape between multiple varieties. This is calculated by dividing the leaf length by the leaf width.

Maturity. Refers to the stage when the plants have mature head formation and are harvestable.

Rogueing. Process in lettuce seed production where undesired plants are removed from a variety because they differ physically from the general, desired expressed characteristics of the new variety.

Plant Part. As used herein, the term "plant part" includes leaves, stems, roots, seed, embryos, pollen, ovules, flowers, root tips, anthers, tissue, cells, axillary buds, and the like.

Plant Cell. As used herein, the term "plant cell" includes plant cells whether isolated, in tissue culture or incorporated in a plant or plant part.

Plant Tissue Color Chart. Refers to the Munsell Color Chart for Plant Tissue which publishes an official botanical color chart quantitatively identifying colors according to a defined numbering system. The Munsell Color Chart for Plant Tissue may be purchased from Munsell Color Services, 617 Little Britain Road, Suite 102, New Windsor, N.Y. 12553-6148, USA, Part Number: 50150.

Lettuce romaine 'River RD.' was originated in year 2000 from a manmade cross between cv. Green Forest (PVP 200000013, U.S. Pat. No. 6,649,816) and a single plant selection out of Cv. El Dorado Cos type. Cv. Green Forest was chosen as a female for its high resistances to tip burn and lettuce drop disease caused by fungus *Sclerotinia minor*. The El Dorado Cos was chosen as a male for its good field tolerance to lettuce downy mildew (*Bremia lactucae*) fungus, resistance to tomato bushy stunt virus and for its thick leaf texture. The cross was made in the greenhouse and initially the collected $F_1$ hybrid plants were genotyped and selected based on the polymorphic SCAR molecular marker W09 which is linked to the Dm1 cluster region (Paran et al. Theor Appl Gen (1993) 85:985-993). The $F_1$ plants were backcrossed to the cv. Green Forest as a recurring parent for two generations. The final backcross seeds were designated as $F_1BC_2$ and the plants were allowed to self in the greenhouse. The $F_2$ progenies were germinated in the greenhouse and the plants were genotyped and selected based on the linkage of polymorphic SCAR molecular marker DMV12 which is linked to the Dm1 cluster region. Plant #37 was selected as homozygous for Dm18 and it was allowed to self in the greenhouse. In 2005 the resulting seeds were planted in D'Arrigo Bros. Ranch 22, Salinas, Calif. In 2006 the progenies were planted D'Arrigo Bros. Ranch 17 Salinas, Calif. and Plant #3 was selected and allowed to self based on the absence of downy mildew on the leaves, survival against *Sclerotinia*, no tip burn, thick leaf texture and heavier weight compared to other plants.

In 2006, the resulting seeds from Plant #3 were planted in the greenhouse and plant #4 was selected and the plant was allowed to self. The seeds of plant #4 were planted in Five Points, California lettuce production field and were allowed to mass.

In 2011 the seeds of previous generation were planted in D'Arrigo Bros. Ranch 11, Soledad, Calif. and plant #3 was selected based on its vigorous growth, the absence of downy mildew on the leaves, survival against Sclerotinia and bushy stunt virus, no tip burn, thick leaf texture and heavier weight compared to other plants. In the following year 2012, the seeds of 2000-126bc$_2$-37-3-4-mass-3 were planted in Sanger, Calif. The plants deemed to be genetically stable and uniform and the plants were massed. In 2013 the seeds were re-planted in Riverdale, Calif. and the plants appeared to be very genetically uniform and the entire population was allowed to self and mass again.

The 2000-126bc$_2$-37-3-4-mass-3-mass seed line has been named 'River RD.' and it is genetically uniform and stable and no genetic variants or off-types have been observed in the last three generations.

'River Road' belongs to the romaine lettuce, *Lactuca sativa* L. varieties. 'River Road' is described as a vigorous romaine cultivar and recommended for the main lettuce growing regions of California for the spring sowing.

A variety description of Lettuce Cultivar River Road is provided in Table 1.

TABLE 1

Variety Description Information

| TRAIT | |
|---|---|
| Plant Type | Cos or Romaine |
| SEED | |
| Color | Black (Grey Brown) |
| Light dormancy | Light Required |
| Heat dormancy | Susceptible |
| COTYLEDON TO FOURTH LEAF STAGE | |
| Shape of Cotyledons | Broad |
| Shape Of Fourth Leaf | Elongated |
| Length/Width Index of Fourth Leaf (Length/Width × 10) | 17 |
| Apical Margin | Entire |
| Basal Margin | Moderately Dentate |
| Undulation | Flat |
| Green Color | Dark Green |
| Anthocyanin Distribution | Absent |
| Anthocyanin Rolling | Absent |
| Anthocyanin Cupping | Uncupped |
| Anthocyanin Reflexing | None |
| MATURE LEAF | |
| Margin Incision Depth (deepest penetration of the margin) | Absent/Shallow (Dark Green Boston) |

TABLE 1-continued

Variety Description Information

| Margin Indentation (finest divisions of the margin) | Entire (Dark Green Boston) |
|---|---|
| Undulations of the Apical Margin | Absent/Slight (Dark Green Boston) |
| Green Color | Very Dark Green |
| Anthocyanin Distribution | Absent |
| Anthocyanin Size | Large |
| Anthocyanin Glossiness | Glossy (Great Lakes) |
| Anthocyanin Blistering | Moderate (Vanguard) |
| Anthocyanin Leaf Thickness | Thick |
| Anthocyanin Trichomes | Absent (Smooth) |
| PLANT | |
| Spread of Frame Leaves | 22 cm |
| Head Size Class | Large |
| Head Per Carton | 24 |
| Head Weight | 0683 grams |
| BUTT | |
| Shape | Rounded |
| Midrib | Flattened (Salinas) |
| CORE | |
| Diameter at Base of Head | 40 mm |
| Core Height From Base of Head to Apex | 74 mm |
| BOLTING | |
| Number of Days from First Water Date to Seed Stalk Emergence (summer conditions) | 69 |
| Bolting Class | Medium |
| Height of Mature Seed Stalk | 89 cm |
| Spread of Bolter Plant | 24 cm |
| Bolter Leaves | Straight |
| Margin | Entire |
| Color | Dark Green |
| Bolter Habit Terminal Inflorescence | Present |
| Bolter Habit Lateral Shoots | Present |
| Bolter Habit Basal Side Shoots | Absent |
| MATURITY | |
| Number of Days from First Water Date to Harvest (spring) | 82 |
| Number of Days from First Water Date to Harvest (summer) | 62 |
| ADAPTATION | |
| Southwest and West Coast | Adapted |
| Season | spring, summer, fall, winter |
| Soil Type | Mineral and Organic |
| VIRAL DISEASES | |
| Big Vein | Moderately Resistant/Moderately Susceptible |
| Lettuce Mosaic | Moderately Resistant/Moderately Susceptible |
| Cucumber Mosaic | Moderately Resistant/Moderately Susceptible |
| Tomato Bushy Stunt, cause of dieback | Resistant |
| Turnip Mosaic | Moderately Resistant/Moderately Susceptible |
| Beet Western Yellows | Moderately Resistant/Moderately Susceptible |
| Lettuce Infectious Yellows | Moderately Resistant/Moderately Susceptible |
| FUNGAL/BACTERIAL DISEASES | |
| Corky Root Rot | Moderately Resistant/Moderately Susceptible |
| Downy Mildew | Resistant |
| Powdery Mildew | Moderately Resistant/Moderately Susceptible |
| *Sclerotinia* Drop | Moderately Resistant/Moderately Susceptible |

TABLE 1-continued

| Variety Description Information | |
|---|---|
| Bacterial Soft Rot (*Pseudomonas* spp. and others) | Moderately Resistant/Moderately Susceptible |
| *Botrytis* (Grey Mold) | Moderately Resistant/Moderately Susceptible |
| Verticillium Wilt | Moderately Resistant/Moderately Susceptible |
| Bacterial Leaf Spot | Moderately Resistant/Moderately Susceptible |
| Anthracnose | Moderately Resistant/Moderately Susceptible |
| PHYSIOLOGICAL STRESSES | |
| Tipburn | Moderately Resistant/Moderately Susceptible |
| Heat | Moderately Resistant/Moderately Susceptible |
| Drought | Moderately Resistant/Moderately Susceptible |
| Cold | Moderately Resistant/Moderately Susceptible |
| Salt | Moderately Resistant/Moderately Susceptible |
| Brown Rib | Moderately Resistant/Moderately Susceptible |

TABLE 1-continued

| Variety Description Information | |
|---|---|
| POST HARVEST STRESS | |
| Pink Rib | Moderately Resistant/Moderately Susceptible |
| Russet Spotting | Moderately Resistant/Moderately Susceptible |
| Rusty Brown Discoloration | Moderately Resistant/Moderately Susceptible |
| Internal Rib Necrosis | Moderately Resistant/Moderately Susceptible |
| Brown Stain | Moderately Resistant/Moderately Susceptible |

Statement of Distinctness

'River RD.' belongs to the romaine lettuce, *Lactuca sativa* L. varieties. 'River RD.' is described as a vigorous romaine cultivar and recommended for the main lettuce growing regions of California and Arizona.

'River RD.' is distinguishable to cv. Zuma based on the followings:

According to the Munsell Color Chart for Plant Tissues, 'River RD.' has glossy leaf color Hue 5 GY, Value 3 and Chroma 4, whereas cv. Zuma has leaf color Hue 5 GY, Value 5 and Chroma 10.

'River RD.' is most similar to cv. Zuma; however, in average 'River RD.' is significantly heavier in plant weight (gm) than cv. Zuma.

'River RD.' is most similar to cv. Zuma; however, in average 'River RD.' is wider in core width (cm) than cv. Zuma.

'River RD.' is most similar to cv. Zuma; however, in average 'River RD.' is significantly longer in leaf length than cv. Zuma.

'River RD.' is most similar to cv. Zuma; however, in average 'River RD.' is significantly wider in leaf width than cv. Zuma.

Table 2 below is the evaluation of 'River Road' and the most similar cultivar, cv. 'Zuma', for several important field traits.

| Variable | Trial | No. Plants/Rep | t*-value | p[t*] | Avg. 'River Road' | Avg. 'Green Forest' |
|---|---|---|---|---|---|---|
| Head Weight (g) | 1 | 20 | 3.6 | 0.000 | 683.5 ± 78.6 | 587.0 ± 87.8 |
| ♣Confidence Interval | | | | | 518.9 to 848.1 | 403.1 to 770.9 |
| | 2 | 20 | 3.8 | 0.000 | 675.5 ± 59.4 | 592.0 ± 76.7 |
| Confidence Interval | | | | | 551.1 to 799.9 | 431.4 to 752.6 |
| Core Width (cm) | 1 | 20 | 4.3 | 0.000 | 4.0 ± 0.21 | 3.8 ± 0.28 |
| Confidence Interval | | | | | 3.6 to 4.5 | 3.4 to 4.2 |
| | 2 | 20 | 4.9 | 0.000 | 4.0 ± 0.16 | 3.7 ± 0.15 |
| Confidence Interval | | | | | 3.7 to 4.4 | 3.5 to 4.1 |
| Leaf Width (cm) | 1 | 20 | 5.7 | 0.000 | 30.7 ± 0.9 | 29.0 ± 0.82 |
| Confidence Interval | | | | | 28.7 to 32.7 | 27.3 to 30.8 |
| | 2 | 20 | 7.8 | 0.000 | 30.4 ± 0.82 | 28.3 ± 0.86 |
| Confidence Interval | | | | | 28.7 to 32.1 | 26.5 to 30.1 |
| Leaf Width (cm) | 1 | 20 | 5.4 | 0.000 | 21.2 ± 1.2 | 19.5 ± 0.67 |
| Confidence Interval | | | | | 18.5 to 24.0 | 18.2 to 20.8 |
| | 2 | 20 | 5.5 | 0.000 | 20.8 ± 1.0 | 19.2 ± 0.76 |
| Confidence Interval | | | | | 18.6 to 23.0 | 17.6 to 20.8 | p[t*] statically different at the 95% confidence level.
Field Trial Locations:
1. D'Arrigo Bros. Ranch 11, Lot 30, Soledad, CA. Water Date: Aug. 17, 2014. Evaluation Date: Oct. 17, 2014.
2. D'Arrigo Bros. Ranch 11, Lot 31, Soledad, CA. Water Date: Feb. 17, 2013. Evaluation Date: May 9, 2013.

Statistical Analysis

Measurable characteristics were assessed in several localities or dates and the results were analyzed separately. Unless otherwise indicated, the statistical analyses were performed using T-test. The results presented in actual t-value and probability values p[t] and are statically different at the 95% confidence level. The standard of deviation for each variety in the comparisons is presented.

This invention is also directed to methods for producing a lettuce plant by crossing a first parent lettuce plant with a second parent lettuce plant, wherein the first parent lettuce plant or second parent lettuce plant is the lettuce plant from cultivar River Road. Further, both the first parent lettuce plant and second parent lettuce plant may be from cultivar River Road. Therefore, any methods using lettuce cultivar River Road are part of this invention, such as selfing, backcrosses, hybrid breeding, and crosses to populations. Plants produced using lettuce cultivar River Road as at least one parent is within the scope of this invention.

In one aspect of the invention, methods for developing novel plant types are presented. In one embodiment the specific type of breeding method is pedigree selection, where both single plant selection and mass selection practices are employed. Pedigree selection, also known as the "Vilmorin system of selection," is described in Fehr, Walter; Principles of Cultivar Development, Volume I, Macmillan Publishing Co., which is hereby incorporated by reference.

In lettuce breeding, lines may be selected for certain desired appropriate characteristics. To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), removal of the anther tubes containing the pollen is performed by procedures well known in the art of lettuce breeding.

In one embodiment, the pedigree method of breeding is practiced where selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny row the preceding generation.

Using this pedigree method, two parents may be crossed using an emasculated female and a pollen donor (male) to produce $F_1$ offspring. To optimize crossing, it is important to note that lettuce is an obligate self-pollinating species. This means that the pollen is shed before stigma emergence, assuring 100% self-fertilization. Since each lettuce flower is an aggregate of about 10-20 individual florets, manual removal of the anther tubes containing the pollen is tedious. As such, methods of removing pollen well known to one of skill in the art, such as misting to wash the pollen off prior to fertilization, may be employed to assure crossing or hybridization. The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

In addition to crossing, selection may be used to identify and isolate new lettuce lines. In lettuce selection, lettuce seeds are planted, the plants are grown and single plant selections are made of plants with desired characteristics. Seed from the single plant selections may be harvested, separated from seeds of the other plants in the field and re-planted. The plants from the selected seed may be monitored to determine if they exhibit the desired characteristics of the originally selected line. Selection work is preferably continued over multiple generations to increase the uniformity of the new line.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding may be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

In one embodiment, promising advanced breeding lines are thoroughly tested and compared to appropriate standards in environments representative of the commercial target area(s). The best lines are candidates for new commercial cultivars; those still deficient in a few traits are used as parents to produce new populations for further selection.

These processes, which lead to the final step of marketing and distribution, usually take several years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of lettuce plant breeding is to develop new, unique and superior lettuce cultivars. In one embodiment, the breeder initially selects and crosses two or more parental lines, followed by repeated selfing and selection, producing many new genetic combinations. The breeder can theoretically generate billions of different genetic combinations via crossing, selfing and mutations. Preferably, each year the plant breeder selects the germplasm to advance to the next generation. This germplasm may be grown under different geographical, climatic and soil conditions, and further selections are then made, during and at the end of the growing season.

In a preferred embodiment, the development of commercial lettuce cultivars requires the development of lettuce varieties, the crossing of these varieties, and the evaluation of the crosses. Pedigree breeding and recurrent selection breeding methods may be used to develop cultivars from breeding populations. Breeding programs may combine desirable traits from two or more varieties or various broad-based sources into breeding pools from which cultivars are developed by selfing and selection of desired phenotypes. The new cultivars may be crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are usually selected. Replicated testing of families, or hybrid combinations involving individuals of these families, often follows in the $F_4$ generation to improve the effectiveness of selection for traits with low heritability. At an advanced stage of inbreeding (e.g., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent may be selected and repeatedly crossed (backcrossed) to the recurrent parent. The resulting plant is expected to have the attributes of the recurrent parent (e.g., cultivar) and the desirable trait transferred from the donor parent.

The single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (Glycine max) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Lettuce is an important and valuable vegetable crop. Thus, a continuing goal of lettuce plant breeders is to develop stable, high yielding lettuce cultivars that are agronomically sound. To accomplish this goal, the lettuce breeder preferably selects and develops lettuce plants with traits that result in superior cultivars.

This invention also is directed to methods for producing a lettuce cultivar plant by crossing a first parent lettuce plant with a second parent lettuce plant wherein either the first or second parent lettuce plant is a lettuce plant of the line River Road. Further, both first and second parent lettuce plants can come from the cultivar River Road. Still further, this invention also is directed to methods for producing a cultivar River Road-derived lettuce plant by crossing cultivar River Road with a second lettuce plant and growing the progeny seed, and repeating the crossing and growing steps with the cultivar River Road-derived plant from 0 to 7 times. Thus, any such methods using the cultivar River Road are part of this invention: selfing, backcrosses, hybrid production, crosses to populations, and the like. All plants produced using cultivar River Road as a parent is within the scope of this invention, including plants derived from cultivar River Road. Advantageously, the cultivar is used in crosses with other, different, cultivars to produce first generation ($F_1$) lettuce seeds and plants with superior characteristics.

As used herein, the term plant includes plant cells, plant protoplasts, plant cell tissue cultures from which lettuce plants can be regenerated, plant calli, plant clumps and plant cells that are intact in plants or parts of plants, such as embryos, pollen, ovules, flowers, seeds, roots, anthers, and the like.

As is well known in the art, tissue culture of lettuce can be used for the in vitro regeneration of a lettuce plant. Tissue culture of various tissues of lettuces and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce lettuce plants having the physiological and morphological characteristics of variety River Road.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as transgenes. Over the last fifteen to twenty years several methods for producing transgenic plants have been developed, and the present invention, in particular embodiments, also relates to transformed versions of the claimed line.

Plant transformation preferably involves the construction of an expression vector that will function in plant cells. Such a vector may comprise DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed lettuce plants, using transformation methods as described below to incorporate transgenes into the genetic material of the lettuce plant(s).

Expression Vectors for Lettuce Transformation

Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Van den Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990<Hille et al., Plant Mol. Biol. 7:171 (1986). Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include .beta.-glucuronidase (GUS), .beta.-galactosidase, luciferase and chloramphenicol, acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984).

Recently, in vivo methods for visualizing GUS activity that do not require destruction of plant tissue have been made available. Molecular Probes publication 2908, Imagene Green™ p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters

Genes included in expression vectors preferably are driven by nucleotide sequence comprising a regulatory element, for example, a promoter. Several types of promoters are now well known in the transformation arts, as are other regulatory elements that can be used alone or in combination with promoters.

As used herein, promoter includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive promoter" is a promoter which is active under most environmental conditions.

A. Inducible Promoters

An inducible promoter is operably linked to a gene for expression in lettuce. Optionally, the inducible promoter is operably linked to a nucleotide sequence encoding a signal sequence which is operably linked to a gene for expression in lettuce. With an inducible promoter the rate of transcription increases in response to an inducing agent. Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter may be operably linked to a gene for expression in lettuce or the constitutive promoter may operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell et al., Nature 313:810-812 (1985) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO96/30530.

C. Tissue-specific or Tissue-preferred Promoters

A tissue-specific promoter may be operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., Structure and Organization of Two Divergent Alpha-Amylase Genes from Barley, Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is lettuce. In another preferred embodiment, the biomass of interest is seed. For transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269: 284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons may involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. Tomato encodes a protein kinase); Mindrinos et al., Cell 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotoch. Biochem. 57:1243 (1993) (nucleotide sequence of Streptomyces nitrosporeus α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera punctata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung lettuce calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb at al., Bio/Technology 10:1436 (1992). The cloning and characterization of a gene which encodes a lettuce endopolygalacturonase-inhibiting protein is described by Toubart et al., Plant J. 2:367 (1992).

R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

S. A lettuce mosaic potyvirus (LMV) coat protein gene introduced into *Lactuca sativa* in order to increase its resistance to LMV infection. See Dinant et al., Molecular Breeding. 1997, 3: 1, 75-86.

2. Genes that Confer Resistance to an Herbicide, for Example:

A. A herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase PAT bar genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in Transgenic Research. 1999, 8: 1, 33-44 that discloses *Lactuca sativa* resistant to glufosinate. European patent application No. 0 333 033 to Kumada at al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Accl-S1, Accl-S2 and Accl-S3 genes described by Marshall et al., Theor. Appl. Genet. 83:435 (1992).

C. A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Increased iron content of the lettuce, for example by transforming a plant with a soybean ferritin gene as described in Goto et al., Acta Horticulturae. 2000, 521, 101-109. Parallel to the improved iron content enhanced growth of transgenic lettuces was also observed in early development stages.

B. Decreased nitrate content of leaves, for example by transforming a lettuce with a gene coding for a nitrate reductase. See for example Curtis et al., Plant Cell Report. 1999, 18: 11, 889-896.

C. Increased sweetness of the lettuce by transferring a gene coding for monellin that elicits a flavor sweeter than sugar on a molar basis. See Penarrubia et al., Biotechnology. 1992, 10: 5, 561-564.

D. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

E. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* .alpha.-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992.

Methods for Lettuce Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-mediated Transformation

One method for introducing an expression vector into plants is based on the natural transformation system of *Agrobacterium*. See, for example, Horsch et al., Science 227:1229 (1985). Curtis et al., Journal of Experimental Botany. 1994, 45: 279, 1441-1449, Torres et al., Plant cell Tissue and Organic Culture. 1993, 34: 3, 279-285, Dinant et al., Molecular Breeding. 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of Agrobacterium vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, Jan.), 165-169 (1993), Aragao, F. J. L., et al. Plant Mol. Biol. 20(2, October), 357-359 (1992), Aragao, F. J. L., et al. Pl. Cell. Rep. 12(9, July), 483-490 (1993). Aragao, Theor. Appl. Genet. 93: 142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992).

Another method for physical delivery of DNA to plants is sonication of target cells. Zhang et al., Bio/Technology 9:996 (1991). Alternatively, liposome or spheroplast fusion has been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994). See also Chupean et al., Biotechnology. 1989, 7: 5, 503-508.

Following transformation of lettuce target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic lettuce line. Alternatively, a genetic trait that has been engineered into a particular lettuce cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term lettuce plant, cultivar or lettuce line is used in the context of the present invention, this also includes any gene conversions of that line. The term gene converted plant as used herein refers to those lettuce plants which are developed by a plant breeding technique called backcrossing wherein essentially all of the desired morphological and physiological characteristics of a cultivar are recovered in addition to the gene transferred into the line via the backcrossing technique. Backcrossing methods can be used with the present invention to improve or introduce a characteristic into the line. The term backcrossing as used herein refers to the repeated crossing of a hybrid progeny back to one of the parental lettuce plants for that line. The parental lettuce plant that contributes the gene for the desired characteristic is termed the nonrecurrent or donor parent. This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a lettuce plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent cultivar are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. Gene traits may or may not be transgenic, examples of these traits include but are not limited to, herbicide resistance, resistance for bacterial, fungal, or viral disease, insect resistance, enhanced nutritional quality, industrial usage, yield stability, yield enhancement, male sterility, modified fatty acid metabolism, and modified carbohydrate metabolism. These genes are generally inherited through the nucleus. Several of these gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of cultivar River Road.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a lettuce plant by crossing a first parent lettuce plant with a second parent lettuce plant wherein the first or second parent lettuce plant is a lettuce plant of cultivar River Road. Further, both first and second parent lettuce plants can come from lettuce cultivar River Road. Thus, any such methods using lettuce cultivar River Road are part of this invention: selfing, backcrosses, hybrid production, crosses to populations, and the like. All plants produced using lettuce cultivar River Road as at least one parent are within the scope of this invention, including those developed from cultivars derived from lettuce cultivar River Road. Advantageously, this lettuce cultivar could be used in crosses with other, different, lettuce plants to produce the first generation ($F_1$) lettuce hybrid seeds and plants with superior characteristics. The cultivar of the invention can also be used for transformation where exogenous genes are introduced and expressed by the cultivar of the invention. Genetic variants created either through traditional breeding methods using lettuce cultivar River Road or through transformation of cultivar River Road by any of a number of protocols known to those of skill in the art are intended to be within the scope of this invention.

The following describes breeding methods that may be used with lettuce cultivar River Road in the development of further lettuce plants. One such embodiment is a method for developing cultivar River Road progeny lettuce plants in a lettuce plant breeding program comprising: obtaining the lettuce plant, or a part thereof, of cultivar River Road, utilizing said plant or plant part as a source of breeding material, and selecting a lettuce cultivar River Road progeny plant with molecular markers in common with cultivar River Road and/or with morphological and/or physiological characteristics selected from the characteristics listed in Table 1. Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method which may be used involves producing a population of lettuce cultivar River Road-progeny lettuce plants, comprising crossing cultivar River Road with another lettuce plant, thereby producing a population of lettuce plants, which, on average, derive 50% of their alleles from lettuce cultivar River Road. A plant of this population may be selected and repeatedly selfed or sibbed with a lettuce cultivar resulting from these successive filial generations. One embodiment of this invention is the lettuce cultivar produced by this method and that has obtained at least 50% of its alleles from lettuce cultivar River Road.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes lettuce cultivar River Road progeny lettuce plants comprising a combination of at least two cultivar River Road traits selected from the group consisting of those listed in Table 1 or the cultivar River Road combination of traits listed above, so that said progeny lettuce plant is not significantly different for said traits than lettuce cultivar River Road as determined at the 5% significance level when grown in the same environmental conditions. Using techniques described herein, molecular markers may be used to identify said progeny plant as a lettuce cultivar River Road progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of lettuce cultivar River Road may also be characterized through their filial relationship with lettuce cultivar River Road, as for example, being within a certain number of breeding crosses of lettuce cultivar River Road. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce cultivar River Road and its progeny. For example, progeny produced by the methods described herein may be within 1, 2, 3, 4 or 5 breeding crosses of lettuce cultivar River Road. The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

Deposits

Applicant(s) have made a deposit of at least 2500 seeds of Lettuce Cultivar River Road with the American Type Culture Collection (ATCC), Manassas, Va. 20110 USA, ATCC Deposit No. PTA-123787. The seeds deposited with the ATCC on Jan. 12, 2017 were taken from the deposit maintained by Central Valley Seeds, 485 Victor Way, Suite 10, Salinas Calif. 93907 since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, samples of the deposit of at least 2500 seeds of cultivar River Road with the American type Culture Collection (ATCC), 10801 University Boulevard, Manassas, Va. 20110-2209. This deposit of the lettuce cultivar River Road will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have satisfied all the requirements of 37 C.F.R. §§1.801-1.809, including providing an indication of the viability of the sample upon deposit. Applicants have no authority to waive any restrictions imposed by law on the transfer of biological material or its transportation in commerce. Applicants do not waive any infringement of their rights granted under this patent or under the Plant Variety Protection Act (7 USC 2321 et seq.).

What is claimed is:

1. A seed of lettuce cultivar designated River Road, wherein a representative sample of seed of said cultivar was deposited under ATCC Accession No. PTA-123787.

2. A lettuce plant, or a part thereof, produced by growing the seed of claim 1.

3. A tissue culture of cells produced from the plant of claim 2, wherein said cells of the tissue culture are produced from a plant part selected from the group consisting of embryo, meristematic cell, leaf, cotyledon, hypocotyl, stem, root, root tip, pistil, anther, flower, seed and pollen.

4. A protoplast produced from the plant of claim 2.

5. A protoplast produced from the tissue culture of claim 3.

6. A lettuce plant regenerated from the tissue culture of claim 3, wherein the plant has all of the morphological and physiological characteristics of cultivar River Road, wherein a representative sample of seed was deposited under ATCC Accession No. PTA-123787.

7. A method for producing a hybrid lettuce seed, wherein the method comprises crossing the plant of claim 2 with a different lettuce plant and harvesting the resultant $F_1$ hybrid lettuce seed.

8. An $F_1$ hybrid lettuce seed produced by the method of claim 7.

9. An $F_1$ hybrid lettuce plant produced by growing said hybrid seed of claim 8.

10. A method of producing a male sterile lettuce plant wherein the method comprises transforming the lettuce plant of claim 2 with a nucleic acid molecule that confers male sterility.

11. A male sterile lettuce plant produced by the method of claim 10.

12. A method for producing an herbicide resistant lettuce plant wherein the method comprises transforming the lettuce plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

13. An herbicide resistant lettuce plant produced by the method of claim 12.

14. A method of producing an insect resistant lettuce plant wherein the method comprises transforming the lettuce plant of claim 2 with a transgene that confers insect resistance.

15. An insect resistant lettuce plant produced by the method of claim 14.

16. The lettuce plant of claim 15 wherein the transgene encodes a *Bacillus thuringiensis* endotoxin.

17. A method of producing a disease resistant lettuce plant wherein the method comprises transforming the lettuce plant of claim 2 with a transgene that confers disease resistance.

18. A disease resistant lettuce plant produced by the method of claim 17.

19. A method of producing a lettuce plant with a value-added trait, wherein the method comprises transforming the lettuce plant of claim 2 with a transgene encoding a protein selected from the group consisting of a ferritin, a nitrate reductase, and a monellin, wherein said protein confers said value-added trait.

20. A lettuce plant with a value-added trait produced by the method of claim 19.

21. A lettuce plant, or a part thereof, having all of the physiological and morphological characteristics of lettuce cultivar River Road, wherein a representative sample of seed of the cultivar was deposited under ATCC Accession No. PTA-123787.

22. A method of introducing a desired trait into lettuce cultivar River Road wherein the method comprises:
  a) crossing a River Road plant grown from River Road seed, wherein a representative sample of seed was deposited under ATCC Accession No. PTA-123787, with a plant of another lettuce cultivar that comprises a desired trait to produce $F_1$ progeny plants, wherein the desired trait is selected from the group consisting of male sterility, herbicide resistance, insect resistance, and resistance to bacterial disease, fungal disease, or viral disease;
  b) selecting one or more progeny plants that have the desired trait to produce selected progeny plants;
  c) crossing the selected progeny plants with the River Road plants to produce backcross progeny plants;
  d) selecting for backcross progeny plants that have the desired trait and all of the physiological and morphological characteristics of lettuce cultivar River Road listed in Table 1 to produce selected backcross progeny plants; and
  e) repeating steps (c) and (d) three or more times in succession to produce selected fourth or higher backcross progeny plants that comprise the desired trait and all of the physiological and morphological characteristics of lettuce cultivar River Road listed in Table 1.

23. A lettuce plant produced by the method of claim 22, wherein the plant has the desired trait and all of the physiological and morphological characteristics of lettuce cultivar River Road listed in Table 1.

24. The lettuce plant of claim 23, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

25. The lettuce plant of claim 23, wherein the desired trait is insect resistance and the insect resistance is conferred by a transgene encoding a *Bacillus thuringiensis* endotoxin.

26. The lettuce plant of claim 23, wherein the desired trait is male sterility and the trait is conferred by a nucleic acid molecule.

* * * * *